(12) United States Patent
Lanter et al.

(10) Patent No.: US 6,858,621 B2
(45) Date of Patent: Feb. 22, 2005

(54) 2-(QUINOLONYL)-FUSED HETEROCYCLES AS ANDROGEN RECEPTOR MODULATORS

(75) Inventors: James C. Lanter, Raritan, NJ (US); Zhihua Sui, Raritan, NJ (US); James J. Fiordeliso, Raritan, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 1 day.

(21) Appl. No.: 10/411,687

(22) Filed: Apr. 11, 2003

(65) Prior Publication Data

US 2004/0014743 A1 Jan. 22, 2004

Related U.S. Application Data

(60) Provisional application No. 60/376,095, filed on Apr. 26, 2002.

(51) Int. Cl.[7] .................. A61K 31/44; A61K 31/435; C07D 455/04; C07D 471/04
(52) U.S. Cl. .................. 514/291; 514/292; 514/293; 546/80; 546/81; 546/82; 546/83; 546/84
(58) Field of Search ................. 514/291, 292, 514/293; 546/80, 81, 82, 83, 84

(56) References Cited

U.S. PATENT DOCUMENTS

| | | | |
|---|---|---|---|
| 5,677,336 A | 10/1997 | Jones et al. | |
| 5,696,130 A | 12/1997 | Jones et al. | |
| 5,716,983 A | 2/1998 | Friebe et al. | |
| 6,017,924 A | 1/2000 | Edwards et al. | |

FOREIGN PATENT DOCUMENTS

| | | |
|---|---|---|
| JP | 3120283 | 5/1991 |
| WO | WO 95/02588 A1 | 1/1995 |
| WO | WO 95/11215 A1 | 4/1995 |
| WO | WO 97/49709 A1 | 12/1997 |
| WO | WO 99/31086 A1 | 6/1999 |
| WO | WO 01/16139 A1 | 3/2001 |
| WO | WO 02/066475 A2 | 8/2002 |
| WO | WO 02/068427 A1 | 9/2002 |

OTHER PUBLICATIONS

Shanazarov, Chemical Abstracts 115:114416, abstract of Khimiya Geterotsiklicheskikh soedinenii, 1991, vol. (1), pp 86–92.*

Sharma, Chemical abstracts 96:6657, abstract of Indian Journal of Chemistry, Secition B, 1981, vol. 20B(9), 744–746.*

Sharma, chemical abstracts 106:84499, abstract of indian journal of chemistry, section b, 1986, vol. 25B(3), pp 271–274.*

Basaria, S. et al.: "Anabolic–Androgenic Steroid Therapy in the Treatment of Chronic Diseases"; The J. of Clin. Endocrinology & Metabolism (2001) 86(11), pp. 5108–5117.

Bashir, M. et al.: "Biological Formation and Chemical Synthesis of 2–Amino–3, 6–Dihydro–3–Methyl–7H–Imidazolo[4,5–f] Quinolin–7–One, the Major Metabolite of the Dietary Carcinogen 2–Amino–3–Methyl–3H–Imidazolo[4,5–f] Quinoline (IQ) by Normal Intestinal Bacteria"; Heterocycles, 1987, vol. 26, No. 11, pp. 2877–2886.

Newling, D.W.W.; "Anti–androgens in the treatment of prostate cancer"; British J. of Urology, 1996, 77, pp. 776–784.

Shahidi, N.T.: "A Review of the Chemistry, Biological Action, and Clinical Applications of Anabolic–Androgenic steroids"; Clin. Therapeutics, 2001, vol. 23, No. 9, pp. 1355–1390.

Uray, G. et al.: "Long–Wavelenth–Absorbing and –Emitting Carbostyrils with High Fluorescence Quantum Yields"; Helvetica Chimica Acta, vol. 82 (1999), pp. 1408–1417.

* cited by examiner

Primary Examiner—D. Margaret Seaman

(57) ABSTRACT

The present invention is directed to novel 2-(quinolonyl)-fused heterocyclyl derivatives of the general formula (I)

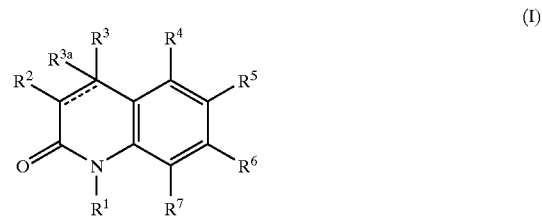

(I)

wherein $R^1$, $R^2$, $R^3$, $R^{3a}$, $R^4$, $R^5$, $R^6$ and $R^7$ are as herein defined, pharmaceutical compositions containing them and their use in the treatment of disorders and conditions modulated by the androgen receptor.

5 Claims, No Drawings

2-(QUINOLONYL)-FUSED HETEROCYCLES AS ANDROGEN RECEPTOR MODULATORS

CROSS REFERENCE TO RELATED APPLICATION

This application claims the benefit of U. S. Provisional Application 60/376,095, filed on Apr. 26, 2002, which is incorporated by reference herein in its entirety.

FIELD OF THE INVENTION

The present invention is directed to novel 2-(quinolonyl)-fused heterocyclyl derivatives, pharmaceutical compositions containing said derivatives and their use in the treatment of disorders and conditions modulated by the androgen receptor. More particularly, the compounds of the present invention are useful in the treatment of prostate carcinoma, benign prostatic hyperplasia (BPH), hisiutism, alopecia, anorexia nervosa, breast cancer, acne, AIDS, cachexia, as a male contraceptive, and as a male performance enhancer.

BACKGROUND OF THE INVENTION

Androgens are the anabolic steroid hormones of animals, controlling muscle and skeletal mass, the maturation of the reproductive system, the development of secondary sexual characteristics and the maintenance of fertility in the male. In women, testosterone is converted to estrogen in most target tissues, but androgens themselves may play a role in normal female physiology, for example, in the brain. The chief androgen found in serum is testosterone, and this is the effective compound in tissues such as the testes and pituitary. In prostate and skin, testosterone is converted to dihydrotestosterone (DHT) by the action of 5α-reductase. DHT is a more potent androgen than testosterone because it binds more strongly to the androgen receptor.

Like all steroid hormones, androgens bind to a specific receptor inside the cells of target tissues, in this case the androgen receptor. This is a member of the nuclear receptor transcription factor family. Binding of androgen to the receptor activates it and causes it to bind to DNA binding sites adjacent to target genes. From there it interacts with coactivator proteins and basic transcription factors to regulate the expression of the gene. Thus, via its receptor, androgens cause changes in gene expression in cells. These changes ultimately have consequences on the metabolic output, differentiation or proliferation of the cell that are visible in the physiology of the target tissue.

Although modulators of androgen receptor function have been employed clinically for some time, both the steroidal (Basaria, S., Wahlstrom, J. T., Dobs, A. S., *J. Clin Endocrino/Metab* (2001), 86, pp5108–5117; Shahidi, N. T., *Clin Therapeutics*, (2001), 23, pp1355–1390), and non-steroidal (Newling, D. W., *Br. J. Urol.*, 1996, 77 (6), pp 776–784) compounds have significant liabilities related to their pharmacological parameters, including gynecomastia, breast tenderness and hepatoxicity. In addition, drug-drug interactions have been observed in patients receiving anticoagulation therapy using coumarins. Finally, patients with aniline sensitivities could be compromised by the metabolites of non-steroidal antiandrogens.

Non-steroidal agonists and antagonists of the androgen receptor are useful in the treatment of a variety of disorders and diseases. More particularly, agonists of the androgen receptor could be employed in the treatment of prostate cancer, benign prostatic hyperplasia, hirsutism in women, alopecia, anorexia nervosa, breast cancer and acne. Antagonists of the androgen receptor could be employed in male contraception, male performance enhancement, as well as in the treatment of cancer, AIDS, cachexia, and other disorders.

Edwards, et.al., in WIPO publication W097/49709 and U.S. Pat. No. 6,017,924 disclose non-steroidal compounds that are high affinity, high selectivity modulators for androgen receptors.

Jones, et.al., in U.S. Pat. No. 5,696,130 disclose tricyclic, non-steroidal compounds that are high affinity, high selectivity modulators for androgen receptors.

Jones et. al., in WIPO publication WO95/11215 and U.S. Pat. No. 5,677,336 disclose non-steroid androgen receptor antagonists.

Friebe et. al., in WIPO publication WO95/02588 and U.S. Pat. No. 5,716,983 disclose coumarins and carbostyrils as $PLA_2$ inhibitors.

Gaster et. al., in WIPO publication WO99/31086 disclose quinolinepiperazine and quinolinepiperidine derivatives and their use as combined 5-HT1A, 5HT1b and 5-HT1D receptor antagonists, useful in the treatment of CNS disorders.

More recently, Higuchi et al., in WIPO publication WO01/16139 disclose non-steroidal compounds that are modulators of androgen receptors.

Nonetheless, there exists a need for small molecule, non-steroidal antagonists of the androgen receptor. We now describe a novel series of (2-quinolonyl)-fused heterocyclic derivatives as androgen receptor modulators.

SUMMARY OF THE INVENTION

The present invention is directed to a compound of formula (Ia)

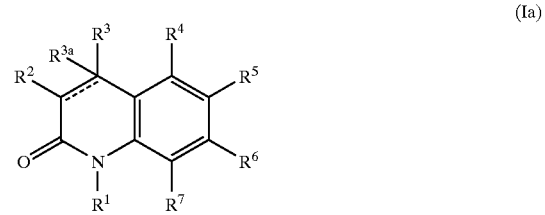

(Ia)

wherein $R^1$ is selected from the group consisting of hydrogen, alkyl alkylcarbonyl, alkylsulfonyl, aminocarbonyl, alkylaminocarbonyl, dialkylaminocarbonyl and alkoxycarbonyl;

$R^2$ is selected from the group consisting of hydrogen, halogen and alkyl;

$R^3$ is selected from the group consisting of hydrogen and fluorinated alkyl;

$R^{3a}$ is absent or hydroxy;

═══represents an optional double bond; (such that when $R^{3a}$ is absent, the double bond extends from the carbon atom of the ring bound to $R^2$ to the carbon atom of the ring bound to $R^3$);

$R^4$ and $R^5$ are taken together with the carbon atoms to which they are bound to form a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group;

$R^6$ and $R^7$ are each independently selected from the group consisting of hydrogen, halogen, hydroxy, carboxy, alkyl, halogenated alkyl, alkoxy, alkoxycarbonyl, alkyl-C(O)—O—, alkyl-C(O)—, alkyl-C(O)—NH—, carboxamide, formyl, cyano, mercapto, thioalkyl, nitro, amino, alkylamino and dialkylamino;

provided that when $R^1$ is hydrogen, $R^2$ is hydrogen, $R^3$ is hydrogen, $R^{3a}$ is absent, ═══ represents a double bond, $R^6$ is hydrogen, $R^7$ is hydrogen and $R^4$ and $R^5$ are taken together with the carbon atoms to which they are bound to form a heterocyclyl group, said heterocyclyl group is not 3,5-dioxin-1-yl, wherein the 3,5-dioxin-1-yl is optionally substituted with one to two alkyl groups;

provided further that when $R^1$ is hydrogen, $R^2$ is hydrogen, $R^3$ is hydrogen, $R^{3a}$ is absent, ═══ represents a double bond, $R^6$ is hydrogen, $R^7$ is hydrogen and $R^4$ and $R^5$ are taken together with the carbon atoms to which they are bound to form a heterocyclyl group, said heterocyclyl group is not 4H-imidazolyl, wherein the 4H-imidazolyl is optionally substituted with one to two alkyl groups;

or a pharmaceutically acceptable salt, ester or prodrug thereof.

The present invention is further directed to a compound of formula (Ib)

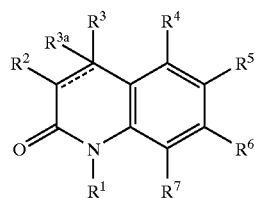

(Ib)

wherein $R^1$ is selected from the group consisting of hydrogen, alkyl, alkylcarbonyl, alkylsulfonyl, aminocarbonyl, alkylaminocarbonyl, dialkylaminocarbonyl and alkoxycarbonyl;

$R^2$ is selected from the group consisting of hydrogen, halogen and alkyl;

$R^3$ is selected from the group consisting of hydrogen and fluorinated alkyl;

$R^{3a}$ is absent or hydroxy;

═══ represents an optional double bond; (such that when $R^{3a}$ is absent, the double bond extends from the carbon atom of the ring bound to $R^2$ to the carbon atom of the ring bound to $R^3$);

$R^4$ and $R^5$ are each independently selected from the group consisting of hydrogen, halogen, hydroxy, carboxy, alkyl, halogenated alkyl, alkoxy, alkoxycarbonyl, alkyl-C(O)—O—, alkyl-C(O)—, alkyl-C(O)—NH—, carboxamide, formyl, cyano, mercapto, thioalkyl, nitro, amino, alkylamino and dialkylamino;

$R^6$ and $R^7$ are taken together with the carbon atoms to which they are bound to form a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group;

provided that when $R^1$ is hydrogen, $R^2$ is hydrogen, $R^3$ is tifluoromethyl, $R^{3a}$ is absent ═══ represents a double bond, $R^4$ is hydrogen, $R^5$ is alkoxy, and $R^6$ and $R^7$ are taken together with the carbon atoms to which they are bound to form a heterocyclyl group, said heterocyclyl group is not 2,4-dioxol-1-yl;

or a pharmaceutically acceptable salt, ester or prodrug thereof.

The present invention is further directed to a compound of formula (Ic)

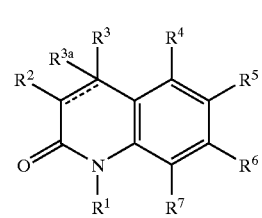

(Ic)

wherein $R^2$ is selected from the group consisting of hydrogen, halogen and alkyl;

$R^3$ is selected from the group consisting of hydrogen and fluorinated alkyl;

$R^{3a}$ is absent or hydroxy;

═══ represents an optional double bond; (such that when $R^{3a}$ is absent, the double bond extends from the carbon atom of the ring bound to $R^2$ to the carbon atom of the ring bound to $R^3$);

$R^4$, $R^5$ and $R^6$ are each independently selected from the group consisting of hydrogen, halogen, hydroxy, carboxy, alkyl, halogenated alkyl, alkoxy, alkoxycarbonyl, alkyl-C(O)—O—, alkyl-C(O)—, alkyl-C(O—NH—, carboxamide, formyl, cyano, mercapto, thioalkyl, nitro, amino, alkylamino and dialkylamino;

$R^7$ and $R^1$ are taken together with the carbon atoms to which they are bound to form a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group;

or a pharmaceutically acceptable salt, ester or prodrug thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders and conditions modulated by the androgen receptor in a subject in need thereof comprising administering to the subject a therapeutically effective amount of any of the compounds or pharmaceutical compositions described above.

An example of the invention is a method for treating an androgen receptor modulated disorder selected from the group consisting of prostate carcinoma, benign prostatic hyperplasia, hirsutism, or for male contraception, in a subject in need thereof comprising administering to the subject an effective amount of any of the compounds or pharmaceutical compositions described above.

Another example of the invention is the use of any of the compounds described herein in the preparation of a medicament for treating: (a) prostate carcinoma, (b) benign prostatic hyperplasia, (c) hirsutism, (d) alopecia, (e) anorexia nervosa, (f) breast cancer, (g) acne, (h) AIDS, (i) cachexia, for (j) male contraception, or for (k) male performance enhancement, in a subject in need thereof.

DETAILED DESCRIPTION OF THE INVENTION

The present invention is directed to compounds of formula (I)

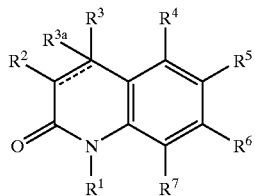

(I)

wherein $R^1$, $R^2$, $R^3$, $R^{3a}$ $R^4$, $R^5$, $R^6$ and $R^7$ are as herein defined, useful for the treatment of disorders and conditions modulated by the androgen receptor.

More particularly, the present invention is directed to compounds of formula (I) wherein one of ($R^4$ and $R^5$) or ($R^6$ and $R^7$) or ($R^7$ and $R^1$) are taken together with the carbon atoms to which they are bound to form a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group.

More particularly, The present invention is a compound of the formula (Ia)

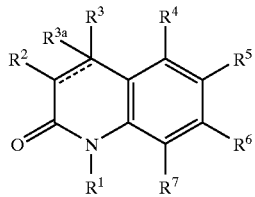

(Ia)

wherein $R^1$, $R^2$, $R^3$, $R^{3a}$ $R^6$ and $R^7$ are as previously defined and wherein $R^4$ and $R^5$ are taken together with the atoms to which they are bound to form a a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group.

In an embodiment of the present invention is a compound of formula (Iaa)

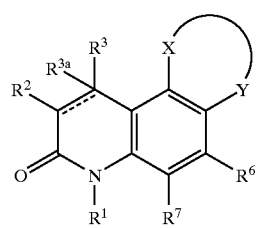

(Iaa)

wherein

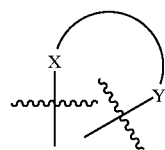

taken together with the atoms to which it is bound represents a five to six membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group; wherein X and Y are each independently selected from the group consisting of O, N and S; and wherein $R^1$, $R^2$, $R^3$, $R^{3a}$ $R^6$ and $R^7$ are as previously defined.

The present invention is further directed to a compound of the formula (Ib)

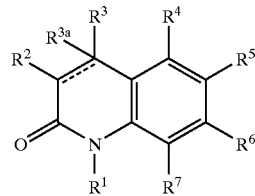

(Ib)

wherein $R^1$, $R^2$, $R^3$, $R^{3a}$ $R^4$ and $R^5$ are as previously defined and wherein $R^6$ and $R^7$ are taken together with the atoms to which they are bound to form a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group.

In an embodiment of the present invention is a compound of formula (Iba)

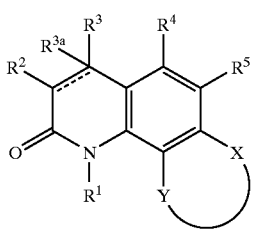
(Iba)

wherein

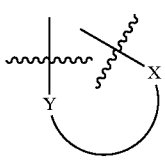

taken together with the atoms to which it is bound represents a five to six membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group; wherein X and Y are each independently selected from the group consisting of O, N and S; and wherein $R^1$, $R^2$, $R^3$, $R^{3a}$ $R^4$ and $R^5$ are as previously defined.

The present invention is further directed to a compound of the formula (Ic)

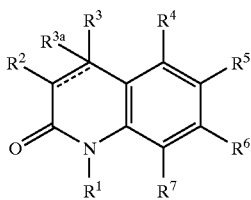
(Ic)

wherein $R^2$, $R^3$, $R^{3a}$ $R^4$, $R^5$ and $R^6$ are as previously defined and wherein $R^7$ and $R^1$ are taken together with the atoms to which they are bound to form a five to eight membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group.

In an embodiment of the present invention is a compound of formula (Ica)

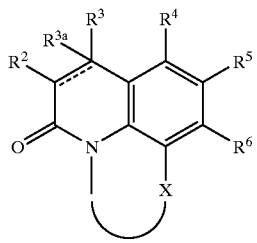
(Ica)

wherein

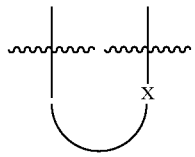

taken together with the atoms to which it is bound represents a five to six membered, heterocyclyl group containing at least two heteroatoms selected from the group consisting of O, N and S; wherein the heterocyclyl group is optionally substituted with one to four substituents independently selected from halogen, alkyl, halogenated alkyl, alkoxy, cyano, alkylcarbonyl, alkylsulfonyl, aminocarbonyl, alkylaminocarbonyl, dialkylaminocarbonyl, alkoxycarbonyl or oxo; provided that when the substituent is oxo, then the substituent is bound to a S atom of the heterocyclyl group; wherein X is selected from the group consisting of O, N and S; and wherein $R^2$, $R^3$, $R^{3a}$ $R^4$, $R^5$ and $R^6$ are as previously defined.

In an embodiment of the present invention $R^1$ is hydrogen. In another embodiment of the present invention $R^2$ is hydrogen. In yet another embodiment of the present invention $R^5$ is hydrogen. In yet another embodiment of the present invention $R^6$ is hydrogen.

In an embodiment of the present invention $R^3$ is halogenated lower alkyl, preferavbly, $R^3$ is trifluoromethyl. In an embodiment of the present invention $R^{3a}$ is absent. In another embodiment $R^{3a}$ is hydroxy. In an embodiment of the present invention $R^{3a}$ is absent and === represents a double bond which extends from the carbon atom of the ring bound to $R^2$ to the carbon atom of the ring bound to $R^3$. In another embodiment of the present invention $R^{3a}$ is hydroxy and === represents a single double bond which extends from the carbon atom of the ring bound to $R^2$ to the carbon atom of the ring bound to $R^3$.

In an embodiment of the present invention $R^4$ is selected from the group consisting of hydrogen, amino, lower alkyl amino or di(lower alkyl)amino. Preferably, $R^4$ is amino. In another embodiment of the present invention $R^7$ is selected form the group consisting of hydrogen and lower alkyl. Preferably, $R^7$ is selected from the group consisting of hydrogen and methyl.

In an embodiment of the present invention $R^4$ and $R^5$ are taken together with the atoms to which they are bound to form a six membered heterocyclyl group containing two heteroatoms selected from the group consisting of O, N and S; wherein the heterocyclyl group is optionally substituted with one to four substituents independently selected from halogen or oxo; provided that when the substituent is oxo, then the substituent is bound to a S atom of the heterocyclyl group. Preferably, $R^4$ and $R^5$ are taken together with the atoms to which they are bound to a heterocyclyl group selected from [1,4]-dioxanyl, 2,2,3,3,-tetrafluoro-[1,4] dioxanyl, thiomorpholinyl, thiomorpholinyl-1,1-dioxide, thiomorpholinyl-1-oxide and morpholinyl.

In an embodiment of the present invention $R^7$ and $R^1$ are taken together with the atoms to which they are bound to form a six membered, heterocyclyl group containing two heteroatoms selected from the group consisting of O, N and S. Preferably, $R^1$ and $R^7$ are taken together with the atoms to which they are bound to form thiomorpholinyl or morpholinyl.

In an embodiment of the present invention $R^6$ and $R^7$ are taken together with the carbon atoms to which they are bound to form a heterocyclyl group, wherein said heterocyclyl group is not 2,4-dioxol-1-yl.

In another embodiment of the present invention $R^4$ and $R^5$ are taken together with the carbon atoms to which they are bound to form a heterocyclyl group, wherein said heterocyclyl group is not 3,5dioxin-1-yl, optionally substituted with one to two alkyl groups.

In yet another embodiment of the present invention $R^4$ and $R^5$ are taken together with the carbon atoms to which they are bound to form a heterocyclyl group, wherein said heterocyclyl group is not 4H-imidazolyl, optionally substituted with one to two alkyl groups.

Representative compounds of the present invention are compounds of formula (Ia) and (Ic) as listed in Tables 1 and 2. The notation "–" indicates the absence of the $R^{3a}$ group and the presence of a double bond extending from thr carbon atom bound to the $R^2$ group to the carbon atom bound to the $R^3$ group, as indicated by the ===== notation.

TABLE 1

| ID # | RWJ # | $R^1$ | $R^3$ | $R^{3a}$ | $R^4 + R^5$ | $R^7$ | Meas. MW |
|------|-------|-------|-------|----------|-------------|-------|----------|
| 1 | 388786 | H | $CF_3$ | — | (1,4-dioxanyl ring) | H | 271.2 |
| 2 | 389316 | H | $CF_3$ | — | (tetrafluoro-1,4-dioxanyl ring) | H | 343.2 |

TABLE 1-continued
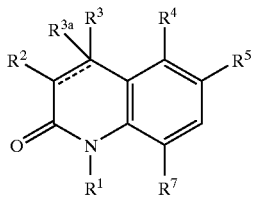
| ID # | RWJ # | R¹ | R³ | R³ᵃ | R⁴ + R⁵ | R⁷ | Meas. MW |
|---|---|---|---|---|---|---|---|
| 3 | 389840 | H | $CF_3$ | — | (CH₂-O-CH₂CH₂-O) ring | $CH_3$ | |
| 4 | 393654 | H | $CF_3$ | OH | (N-CH₂CH₂-S) ring | H | |
| 5 | 394022 | H | $CF_3$ | — | (N-CH₂CH₂-S) ring | H | 286.3 |
| 6 | 394135 | H | $CF_3$ | — | (N-CH₂CH₂-SO₂) ring | H | 318.3 |
| 7 | 394175 | H | $CF_3$ | — | (N-CH₂CH₂-SO) ring | H | |
| 8 | 400494 | H | $CF_3$ | — | (N-CH₂CH₂-O) ring | H | 270.2 |

TABLE 1-continued

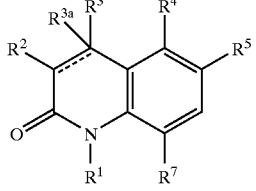

| ID # | RWJ # | R¹ | R³ | R³ᵃ | R⁴ + R⁵ | R⁷ | Meas. MW |
|---|---|---|---|---|---|---|---|
| 13 | 400215 | H | CF₃ | OH | | H | 288.2 |

TABLE 2

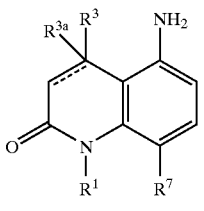

| ID # | RWJ # | R³ | R³ᵃ | R¹ + R⁷ | MW MH⁺ |
|---|---|---|---|---|---|
| 9 | 398184 | CF₃ | OH | (S-containing ring) | 304.29 |
| 10 | 398196 | CF₃ | — | (S-containing ring) | 286.28 |
| 14 | 402195 | CF₃ | — | (O-containing ring) | |

As used herein, "halogen" shall mean chlorine, bromine, fluorine and iodine.

As used herein, the term "alkyl" whether used alone or as part of a substituent group, include straight and branched chains comprising one to six carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1–4 carbon atoms.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocylic aromatic groups such as phenyl, naphthyl, and the like.

As used herein, unless otherwise noted, "aralkyl" shall mean any lower alkyl group substituted with an aryl group such as phenyl, naphthyl and the like. For example, benzyl, phenylethyl, phenylpropyl, naphthylmethyl, and the like.

As used herein, unless otherwise noted, the term "cycloalkyl" shall mean any stable 3–8 membered monocyclic, saturated ring system, for example cyclopropyl, cyclobutyl, cyclopentyl, cyclohexyl, cycloheptyl and cyclooctyl.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated, partially unsaturated or partially aromatic ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, [1,4-dioxanyl], and the like. Preferred heterocycloalkyl groups include [1,4 ]dioxanyl, morpholinyl, thiomorpholinyl and piperadinyl.

As used herein, unless otherwise noted, the term "heterocycle" or "heterocyclyl" shall mean any heteroaryl or heterocycloalkyl ring as herein defined.

As used herein, particularly in the schemes below, the symbol

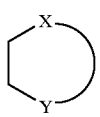

shall represent a five to eight membered ring structure wherein X and Y are independently selected from the group consisting of O, N and S. Suitable examples include imidazolidine, oxazolidine, thiazolidine, 1,3-thiolane, 1,3-oxathiolane, 1,3-dioxalane, piperazine, morpholine, thiomorpholine, 1,4-dioxane, 1,4-dithiane, 1,4-oxathiane, [1,4]dioxepane, [1,4]oxazepane, [1,4]oxathiepane, [1,4]diazepane, [1,4]thiazepane, [1,4]dithiepane, [1,4]dioxocane, [1,4]oxazocane, [1,4]oxathiocane, [1,4]diazocane, [1,4]thiazocane, [1,4]dithiocane, and the like.

As used herein, the notation "*" shall denote the presence of a stereogenic center.

When a particular group is "substituted" (e.g., aryl, heteroaryl, heterocycloalkyl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment Thus, for example, a "phenylalkylaminocarbonylalkyl" substituent refers to a group of the formula

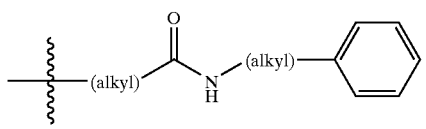

Unless otherwise noted, wherein $R^4$ and $R^5$ or $R^6$ and $R^7$ or $R^7$ and $R^1$ are taken together with the atoms to which they are bound to form a ring structure, the ring structure shall be named such that the point of attachment for $R^4$, $R^5$, $R^6$ or $R^7$, respectively, is numbered as position 1, with the remainder of the ring structure numbered in a clockwise manner. For example, for the compound

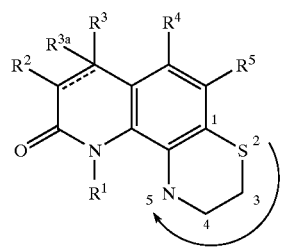

$R^6$ and $R^7$ are taken together with the atoms to which they are bound to form 2-thiomorpholinyl, where the numbering is as indicated.

Abbreviations used in the specification, particularly the Schemes and Examples, are as follows:

| | | |
|---|---|---|
| DBU | = | 1,8-Diazabicyclo[5.4.0]undec-7ene |
| DDT | = | Dithiothreitol |
| DIEA | = | Diisopropyl ethyl amine |
| DMF | = | Dimethyl formamide |
| DMSO | = | Dimethylsulfoxide |
| EDTA | = | Ethylene Diamine Tetraacetic Acid |
| PEG | = | Polyethylene glycol |
| TED Buffer | = | Tris-EDTA-DTT |
| THF | = | Tetrahydrofuran |
| Tris HCl | = | Tris[hydroxymethyl]aminomethyl hydrochloride |

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compounds of the present invention may be prepared from known compounds or compounds prepared by known methods. For example, the compounds of formula (I) of the present invention wherein two adjacent R groups (i.e. $R^4$ and $R^5$; $R^6$ and $R^7$; or $R^7$ and $R^1$) are taken together to form a six membered heterocyclyl ring may be prepared from the starting materials labeled (S1) through (S9).

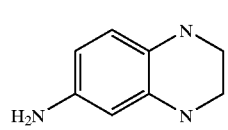

(S1)

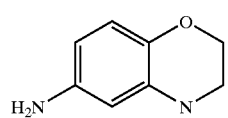

(S2)

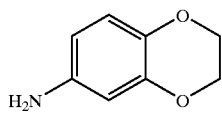

(S3)

Compounds of formula (S1), (S2) and (S3) are known compounds.

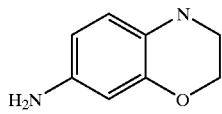

(S4)

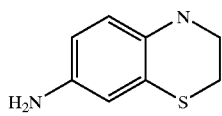

(S5)

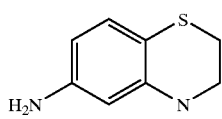

(S6)

Compounds of formula (S4), (S5) and (S6) may be prepared from known compounds by known methods. For example, compounds (S4) and (S6) may be prepared by known methods from 7-amino-4H-benzo[1,4]oxazine-3-one and 6-amino4H-benzo[1,4]thiazin-3-one, respectively. The compound of formula (S5) may be prepared by known methods from 7-amino-2-methyl-4H-benzo[1,4]thiazin-3-one.

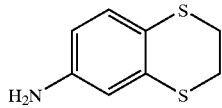

(S7)

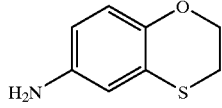

(S8)

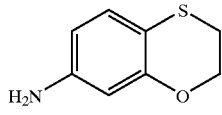

(S9)

Compounds of formula (S7), (S8) and (S9) may be prepared from known compounds. For example, the compounds of formula (S7), (S8) and (S9) may be prepared from the corresponding 2,3-dihydro-benzo[1,4]dithiine and 2,3-dihydro-benzo[1,4]oxazthiine, respectively, by nitrating and then reducing the nitro group to the corresponding amine.

One skilled in the art will recognize that substitution of the heterocyclyl ring portion of any of the compounds of formula (Ia), (Ib) and/or (Ic) may optionally be introduced prior to cyclization of the heterocyclyl protion by known methods.

Compounds of formula (Ia) and (Ic) may be prepared according to the process outlined in Scheme 1.

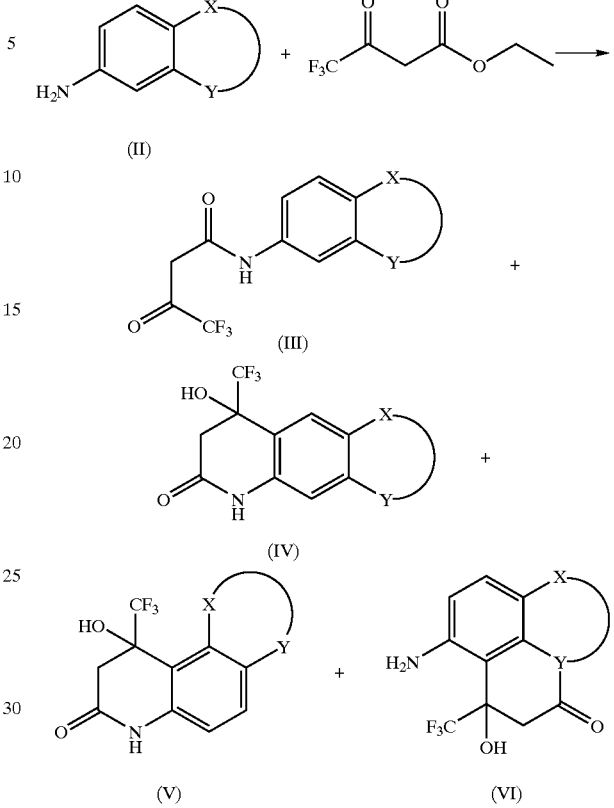

Scheme 1

More particularly, a suitably substituted compound of formula (II), a known compound or compound prepared by known methods, is reacted with 1,1,1-trifluoro-heptane-2,4-dione, in an organic solvent such as toluene, xylene, decalin, and the like, in the presence of an organic base such as pyridine, DBU, DIEA, $K_2CO_3$, and the like, to yield a mixture of compounds of formula (III), (IV) and (V), and when Y is N, compound of formula (VI). (Wherein the compound of formula (V) is an intermediate in the preparation of the compound of formula (Ia), a compound of formula (I) wherein $R^4$ and $R^5$ are taken together to form a heterocyclyl ring; and wherein Y is N, the compound of formula (VI) is an intermediate in the preparation of the compound of formula (Ic), a compound of formula (I) wherein $R^7$ and $R^1$ are taken together to forma heterocyclyl ring.)

Preferably, the mixture of compounds of formula (III), (IV), (V) and (VI) are separated to yield the desired component.

One skilled in the art will recognize that compounds of formula (Ia) and (Ic) wherein $R^{3a}$ is absent may be prepared from the corresponding compound of formula of (Ia) or (Ic) wherein $R^{3a}$ is hydroxy, by reacting with an acid such as sulfuric acid, hydrochloric acid, and the like. Alternatively, when $R^{3a}$ is hydroxy group, the hydroxy group may be removed by known dehydration methods.

One skilled in the art will further recognize that compounds of formula (Ia) and (Ic) wherein $R^3$ is a halogenated alkyl other than trifluoromethyl may be similarly prepared according to the process outlined above with substitution of an suitably substituted reagent for the 1,1,1-trifluoro-heptane-2,4-dione.

One skilled in the art will further recognize that compounds of formula (Ia) wherein $R^1$, $R^6$ and/or $R^7$ are other than hydrogen, and/or compounds of formula (Ic) wherein $R^4$, $R^5$ and/or $R^6$ are other than hydrogen, may be prepared by known methods, for example by employing a suitably substituted starting material or reagent. Additionally, $R^1$ groups other than hydrogen may be incorporated into the compound of formula (I) by known methods after formation of the corresponding compound of formula (I) wherein $R^1$ is hydrogen.

Compounds of formula (Ib) wherein $R^6$ and $R^7$ are taken together to form a six membered heterocyclyl ring, may be prepared according to the process outline in Scheme 2.

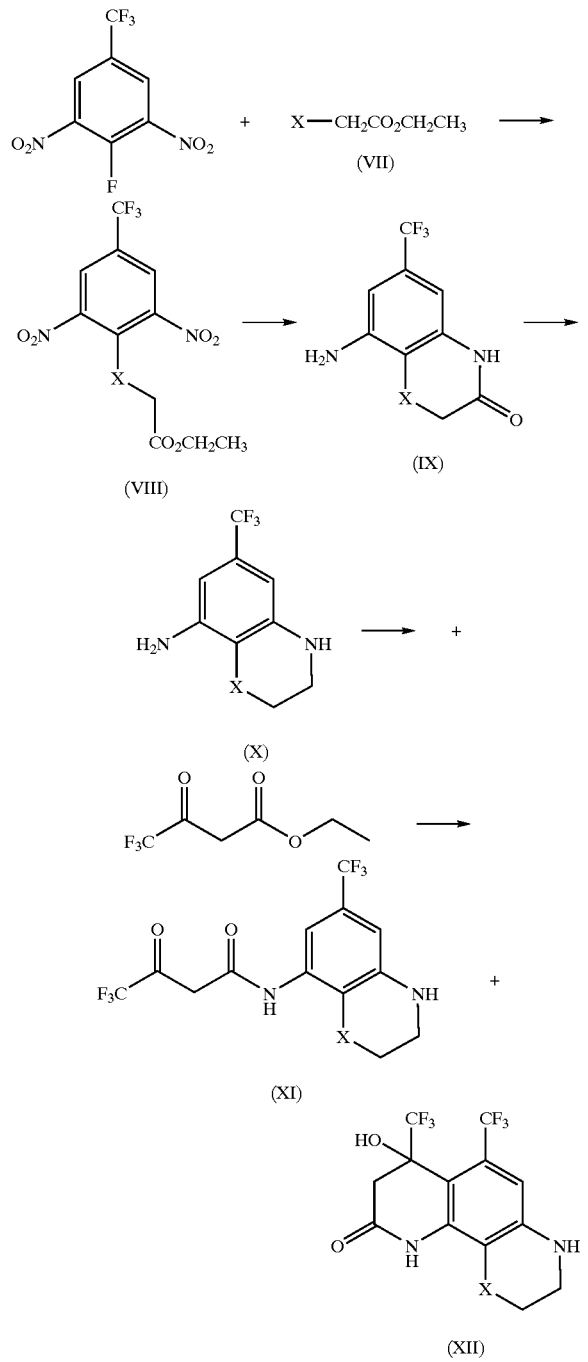

Accordingly, 2-fluoro-1,3-dinitro-5-trifluoromethyl-benzene, a known compound, is reacted with a suitably substituted compound of formula (VII), a known compound or compound prepared by known methods, in the presence of a base such as NaH, $K_2CO_3$, and the like, in an organic solvent such as DMF, DMSO, and the like, to yield the corresponding compound of formula (VIII).

The compound of formula (VIII) is reduced by known methods, for example, by hydrogenation in the presence of a catalyst such as Pd on Carbon, in an organic solvent such as methanol, ethanol, ethyl acetate, and the like, to yield the corresponding compound of formula (IX).

The compound of formula (IX) is selectively reduced with a suitable reducing agent such as borane, LiAH, and the like, in an organic solvent such as THF, diethyl ether, and the like, to yield the corresponding compound of formula (X).

The compound of formula (X) is reacted with 1,1,1-trifluoro-heptane-2,4-dione, in an organic solvent such as toluene, xylene, decalin, and the like, in the presence of an organic base such as pyridine, DBU, DIEA, $K_2CO_3$, and the like, to yield a mixture of the corresponding compound of formula (XI) and the corresponding compound of formula (XII). (Wherein the compound of formula (XII) is a compound of formula (Ib) or an intermediate in the formation of a compound of formula (Ib).)

Preferably, the compound of formula (XI) and the compound of formula (XII) are separated by known methods.

One skilled in the art will recognize that compounds of formula (Ib) wherein $R^6$ and $R^7$ are taken together to form a six membered heterocyclic ring, other than those described above, may be similarly prepared by known methods, by substitution of suitably substituted reagents of the formula (XIII)

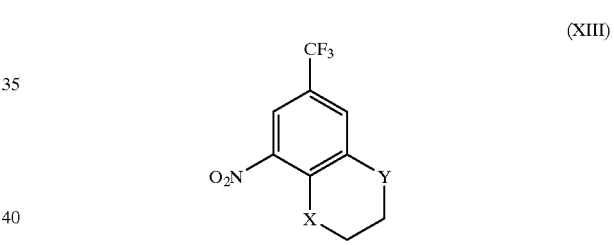

wherein X and Y are independently selected from O, N and S, for the compound of formula (X) in Scheme 2.

Compounds of formula (Ib) wherein $R^{3a}$ is absent may be prepared from the corresponding compound of formula of (Ib) wherein $R^{3a}$ is hydroxy, by known methods, for example by reacting with an acid such as sulfuric acid, hydrochloric acid, and the like. Alternatively, when $R^{3a}$ is hydroxy group, the hydroxy group may be removed by known dehydration methods.

One skilled in the art will further recognize that compounds of formula (Ib) wherein $R^3$ is a halogentaed alkyl other than trifluoromethyl may be similarly prepared according to the process outlined above with substitution of an suitably substituted reagent for the 1,1,1-trifluoro-heptane-2,4-dione.

One skilled in the art will further recognize that compounds of formula (Ib) wherein $R^1$, $R^4$ and/or $R^5$ are other than hydrogen, may be prepared by known methods, for example by employing a suitably substituted starting material or reagent. Additionally, $R^1$ groups other than hydrogen may be incorporated into the compound of formula (I) by known methods after formation of the corresponding compound of formula (I) wherein $R^1$ is hydrogen.

One skilled in the art will recognize that compounds of formula (Ia), (Ib) and/or (Ic) wherein two adjacent R groups (i.e. $R^4$ and $R^5$; $R^6$ and $R^7$; or $R^7$ and $R^1$) are taken together to form a five, seven or eight membered heterocyclyl ring may be prepared according to the process outlined in Scheme(s) 1 and 2, with suitable selected and substitution of compounds of formula (II) and the compound of formula (VII), respectively. For example, the compound of formula (II) may be selected such that the

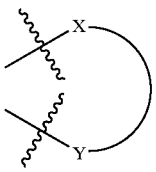

portion of the compound of formula (II) is a chain of 4 to 6 atoms. Similarly, the compound of formula (VII) may be chosen such that the —$CH_2$— portion of the compound of formula (VII) found between the X and $CO_2$ portions is replaced with a —$CH_2CH_2$— portion or a —$CH_2CH_2CH_2$— portion to yield the 7 membered or eight membered group respectively.

One skilled in the art will further recognize that compounds of formula (Ia), (Ib) and/or (Ic) wherein $R^4$ and $R^5$ or $R^6$ and $R^7$ or $R^7$ and $R^1$ are taken together to form a five membered heterocyclyl group may be similarly prepared from suitably substituted known starting materials, for example, amine substituted benziimidazolyl, benzthiazolyl, and the like.

The following Examples are set forth to aid in the understanding of the invention, and are not intended and should not be construed to limit in any way the invention set forth in the claims which follow thereafter.

EXAMPLE 1

6-Nitro-4H-benzo[1,4]oxazin-3-one

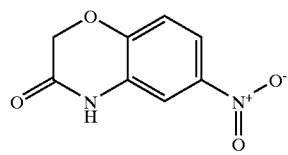

A suspension of 2-amino4-nitrophenol (7.7 g, 50 mmol) was prepared in 125 mL chloroform. To this suspension was added benzyltriethylammonium chloride (11.4 g, 50 mmol) and sodium bicarbonate (16.80 g, 200 mmol) and the suspension cooled in an ice bath. A solution of chloroacetyl chloride (4.8 mL, 60 mmol) in chloroform (10 mL) was added. The solution was stirred overnight at room temperature, then refluxed for 3 hours and again let sit overnight at room temperature. The solvent was removed under vacuum and water was added to the residue. The solid was filtered, washed with water, and recrystallized from ethanol. The recrystallized solid was filtered and washed with cold ethanol and then dried, to yield 6-nitro-4-H-benzo[1,4]oxazin-3-one as a solid product. Some additional product precipitated from the ethanol filtrate as a second crop and was recovered by filtration.

Yield: 5.5 g, 57%

EXAMPLE 2

∂6-Nitro-3,4-dihydro-2H-benzo[1,4]oxazine

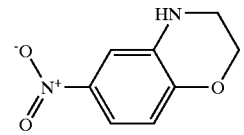

To a suspension of 6-nitro-4-H-benzo[1,4]oxazin-3-one (7.84 g, 40.38 mmol) in tetrahydrofuran (100 mL) was added a solution of 2.0M borane-methyl sulfide complex in tetrahydrofuran (91 mL, 181 mmol). The mixture was heated to reflux for 4.5 hours then allowed to stir overnight at room temperature. Methanol was added slowly to react with unreacted borane-methyl sulfide complex, which resulted a violent evolution of gas. When this subsided, excess methanol was added and the solution heated to reflux. After 2 hours the solution was cooled, the solvent evaporated under vacuum, and the residue triturated with ethyl acetate/hexane. An orange solid was filtered off which was rinsed with hexane, to yield 6-nitro-3,4-dihydro-2H-benzo[1,4]oxazine as a solid product. More of the solid was recovered as a second crop from the filtrate.

Yield: 5.6 g, 77%

EXAMPLE 3

3,4-Dihydro-2H-benzo[1,4]oxazin-6-ylamine

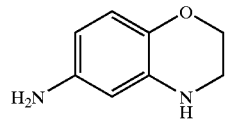

A solution of 6-nitro-3,4-dihydro-2H-benzo[1,4]oxazine (1.8 g, 10.0 mmol) in methanol (150 mL) was hydrogenated on a Parr hydrogenator for 6 hours with 10% palladium on carbon (1.06 g) as a catalyst. The reaction mixture was filtered through Celite to remove the catalyst and the Celite rinsed with methanol. The filtrate was evaporated under vacuum to yield 3,4-dihydro-2H-benzo[1,4]oxazin-6-yl amine as a solid product.

Yield: 1.48 g, 99%

EXAMPLE 4

5-Hydroxy-5-trifluoromethyl-3,4,5,8-tetrahydro-2H, 6H-1-oxa-4,8-diazaphenanthren-7-one 7-amino-6-hydroxy-6-trifluoromethyl-2,3,5,6-tetrahydro-1-oxa- 3a-aza-phenalen-4-one 6-ethyoxy-8-trifluoromethyl-3,4-dihydro-2H-1-oxa-4,5-diaza-anthracene

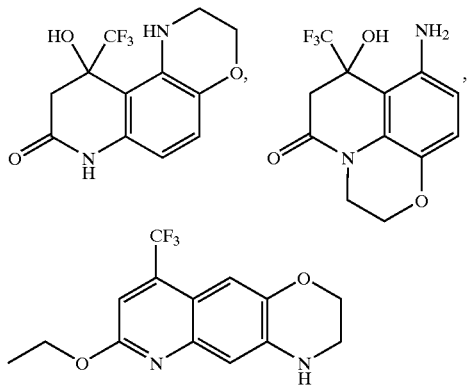

To a solution of 3,4-dihydro-2H-benzo[1,4]oxazin-6-yl amine (0.56 g, 3.73 mmol) in toluene (20 mL) was added ethyl 4,4,4-trifluoroacetoacetate (0.55 mL, 3.73 mmol) and 4 drops of pyridine. The solution was heated to reflux for 6 hours, then allowed to stir overnight at room temperature. The solvent was removed under vacuum and the residue triturated with diethyl ether. The solid was filtered off and washed with diethyl ether to yield a gray solid which was determined by $^1$HNMR to contain crude N-(3,4-dihydro-2H-benzo[1,4]oxazin-6-yl)-4,4,4-trifluoro-3-oxo-butyramide. The rest of the material in the filtrate was also determined by $^1$HNMR to be crude N-(3,4-dihydro-2H-benzo[1,4]oxazin-6-yl)-4,4,4-trifluoro-3-oxo-butyramide, but much less pure than the gray solid filtered off. The mixture was recovered by evaporating the ether. This mixture (0.8 g) was stirred in of concentrated sulfuric acid (8 mL) overnight at room temperature. The reaction mixture was then poured onto ice and neutralized by adding 1N sodium carbonate. The resulting solution was extracted three times with ethyl acetate, the extracts dried over magnesium sulfate, filtered and evaporated under vacuum to yield a brown oil. The brown oil (crude material) was purified by column chromatography on a Biotage system eluting with 4% methanol/ethyl acetate to yield 8-trifluoromethyl-3,4-dihydro-2H,5H-1-oxa-4,5diaza-anthracen-6-one as the main product.

Yield: 67 mg, 9% (RWJ-392715)

linear, MH$^+$=289

Some early, impure fractions were purified again by chromatography eluting with 20% ethyl acetate/hexane to yield:

(a) 6-ethoxy-8-trifluoromethyl-3,4-dihydro-2H-1-oxa-4,5-diaza-anthracene

Yield: 24.3mg, 3%, MH$^+$=299

(b) 5-hydroxy-5-trifluoromethyl-3,4,5,8-tetrahydro-2H,6H-1-oxa-4,8-diaza-phenanthren-7-one Yield: 230 mg, 29%

(c) mixture of 7-amino-6-hydroxy-6-trifluoromethyl-2,3,5,6-tetrahydro-1-oxa-3a-aza-phenalen-4-one and 5-hydroxy-5-trifluoromethyl-3,4,5,8-tetrahydro-2H, 6H-1-oxa-4,8-diaza-phenanthren-7-one Yield: 0.2 g, 25%

EXAMPLE 5

5-Trifluoromethyl-3,4-dihydro-2H,8H-1-oxa-4,8-diaza-phenanthrene-7-one

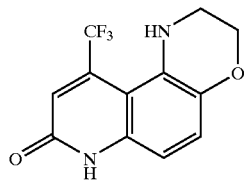

A solution of 5-hydroxy-5-trifluoromethyl-3,4,5,8-tetrahydro-2H,6H-1-oxo-4,8-diaza-phenanthren-7-one compound in concentrated sulfuric acid (3mL) was prepared and allowed to stir overnight, then heated to 140° C. for 2 hours. The solution was added to ice, neutralized with 1M sodium carbonate, and extracted 3 times with ethyl acetate. The organic extracts were dried over magnesium sulfate, filtered, and the filtrate evaporated under vacuum to yield 5-trifluoromethyl-3,4-dihydro-2H,8H-1-oxa-4,8-diaza-phenanthren-7-one as a yellow solid.

Yield: 0.16 g, 84%

MH$^+$=271

EXAMPLE 6

7-Amino-6-trifluoromethyl-2,3-dihydro-1-oxa-3a-aza-phenalen-4-one

5-Trifluoromethyl-3,4-dihydro-2H,8H-1-oxa-4,8-diaza-phenanthren-7-one

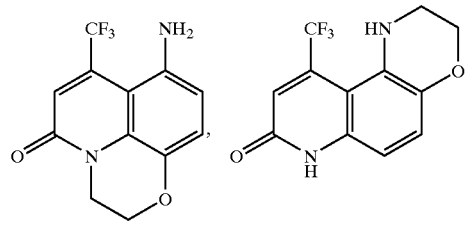

Impure 7-amino-6-hydroxy-6-trifluoromethyl-2,3,5,6-tetrahydro-1-oxa-3a-aza-phenalen-4-one (0.2 g) was heated to 140° C. for 1.5 hours then stirred at room temperature overnight. The reaction mixture was poured onto ice, made basic with 1M sodium carbonate, extracted three times with ethyl acetate, dried the organic extracts over magnesium sulfate, filtered, evaporated to a yellow solid. The yellow solid (crude material) was purified using the Biotage 40S system eluting with 30% ethyl acetate/hexane to yield 7-amino-6-trifluoromethyl-2,3-dihydro-1-oxa-3a-aza-phenalen-4-one Yield: 37.2mg, 20%

MH$^+$=271 and when eluted with 50% ethyl acetate/hexane to yield 5-trifluoromethyl-3,4-dihydro-2H,8H-1-oxa-4,8-diaza-phenanthren-7-one Yield: 80mg, 42%

EXAMPLE 7

(2,4-Dinitro-phenylsulfanyl)-acetic acid ethyl ester

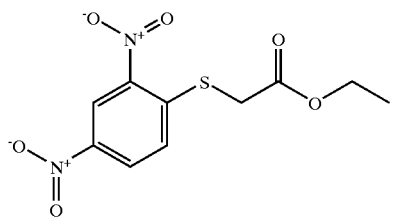

A solution of 2,4-dinitrofluorobenzene (15.7 mL, 124.8 mmol) in tetrahydrofuran (32 mL) was prepared. To this solution, triethylamine (17.4 mL, 124.8 mmol) was added and the solution cooled in an ice bath. To the solution was then added a solution of ethyl 2-mercaptoacetate (15 g, 124.8 mmol) in tetrahydrofuran (10 mL) slowly, dropwise. The reaction mixture was allowed to warm to room temperature overnight under nitrogen atmosphere. The solution was then poured onto 200 mL of ice and stirred until the ice melted. The resulting solution was extracted twice with ethyl acetate and the organic layers were washed with water, brine, and dried over magnesium sulfate. The magnesium sulfate was filtered off and the filtrate evaporated under vacuum to yield a brown oil. The oil was triturated with hexane and a small amount of diethyl ether. A sticky solid was filtered off and then washed with hexane to yield (2,4-dinitro-phenylsulfanyl)-acetic acid ethyl ester.

Yield: 37.2 g

EXAMPLE 8

6-Amino-4H-benzo[1,4]thiazin-3-one

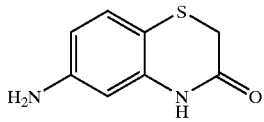

A mixture of iron (30.2 g, 540 mmol), glacial acetic acid (2 mL), and water (40 mL) was prepared in a 500 mL 3-necked round bottom flask equipped with a dropping funnel and an overhead stirrer. A solution of (2,4-dinitro-phenylsulfanyl)-acetic acid ethyl ester (11.79 g, 41.2 mmol) in glacial acetic acid (40 mL) and ethyl acetate (40 mL) was added dropwise. After addition the dropping funnel was replaced with a condenser and the solution heated at 80° C. for 3.5 hrs, then allowed to stir overnight at room temperature. The mixture was filtered through Celite and the Celite washed with ethyl acetate and water. The layers were separated in a separatory funnel and the aqueous layer extracted twice with ethyl acetate. The organic layers were washed with water, twice with saturated sodium bicarbonate, then dried over magnesium sulfate, filtered, and evaporated under vacuum to yield a 6-amino-4H-benzo[1,4]thiazin-3-one as a brown solid.

Yield: 3.9 g, 52%

EXAMPLE 9

3,4-Dihydro-2H-benzo[1,4]thiazin-6-ylamine

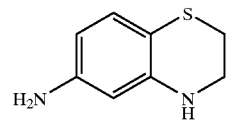

A solution of 6-amino-4H-benzo[1,4]thiazin-3-one (1.95 g, 10.82 mmol) in 50 mL tetrahydrofuran (50 mL) was prepared. To this solution was added 2M borane-dimethyl sulfide complex (24 mL) in tetrahydrofuran (24 mL, 48.69 mmol). The solution was heated at reflux under a nitrogen atmosphere for 5 hours, then cooled to room temperature overnight. Methanol was added in portions to quench unreacted borane-dimethyl sulfide complex. The solution was then refluxed for 0.5 hrs. The solvent was removed under vacuum and the residue purified by column chromatography eluting with 20, 40, and 60% ethyl acetate/hexane. The cleanest fractions containing product were collected to yield 3,4-dihydro-2H-benzo[1,4]thiazin-6-ylamine as a green oil.

Yield: 1.0 g, 58%

EXAMPLE 10

5-Hydroxy-5-trifluoromethyl-3,4,5,8-tetrahydro-2H, 6H-1-thia-4,8-diaza-phenanthren-7-one 8-hydroxy-8-trifluoromethyl-3,4,7,8-tetrahydro-2H, 5H-1-thia-4,5-diaza-anthracen-6-one

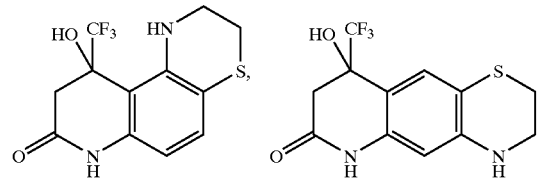

A solution of 3,4-dihydro-2H-benzo[1,4]thiazin-6-ylamine (0.95 g, 5.72 mmol), ethyl 4,4,4-trifluoroacetoacetate (0.84 mL, 5.72 mmol), and 4 drops of pyridine in 20 mL of toluene was prepared and then heated to reflux. Some solid was observed to precipitate out of solution. After 5 hours, the reaction mixture was cooled and the solvent evaporated under vacuum. The material was purified using the Biotage system eluting with 50% and 75% ethyl acetate/hexane to yield two products: 5-hydroxy-5-trifluoromethyl-3,4,5,8-tetrahydro-2H,6H-1-thia-4,8-diaza-phenanthren-7-one Yield: 0.72 g $MH^+$=305 and 8-hydroxy-8-trifluoromethyl-3,4,7,8-tetrahydro-2H, 5H-1-thia-4,5-diaza-anthracen-6-one Yield: 80 mg $MH^{30}$ =305

EXAMPLE 11

5-Trifluoromethyl-3,4-dihydro-2H,8H, 1-thia-4,8-diaza-phenanthren-7-one

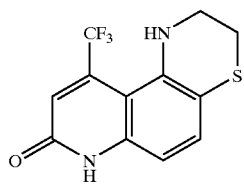

The dehydration of 5-hydroxy-5-trifluoromethyl-3,4,5,8-tetrahydro-2H,6H-1-thia-4,8-diaza-phenanthren-7-one (69 mg, 0.23 mmol) was carried out in concentrated sulfuric acid at 150° C. The solution was cooled to about rrom temperature, added to ice water, made basic with 1M sodium carbonate, extract with ethyl acetate three times, the organic layers washed with brine, dried over sodium sulfate, filtered and the filtrate evaporated to yield 5-trifluoromethyl-3,4-dihydro-2H,8H-1-thia-4,8-diaza-phenanthren-7-one as a green solid.

Yield: quantitative yield $MNa^+=309$

EXAMPLE 12

5-Hydroxy-1,1-dioxo-5-trifluoromethyl-1,3,4,5,6,8-hexahydro-2H-1$\Xi^6$-thia-4,8- diaza-phenanthren-7-one

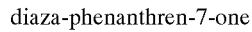

A solution of 5-trifluoromethyl-3,4-dihydro-2H,8H-1-thia-4,8-diaza-phenanthren-7-one (0.16 g, 0.559 mmol) was prepared by dissolving it in methanol (20 mL) and dichloromethane (2 mL). To this solution was added oxone (1.03 g, 1.677 mmol) dissolved in a minimal amount of water. The solution became cloudy so a small amount of THF was added and the mixture was allowed to stir overnight at room temperature. The solution was evaporated under reduced pressure. Ethyl acetate was then added to the residue. The solution was washed twice with water, dried over magnesium sulfate, filtered, and concentrated under reduced pressure. The material was purified using the Biotage 40S system eluting with 60% and 70% ethyl acetate/hexane to yield 5-hydroxy-1,1-dioxo-5-trifluoromethyl-1,3,4,5,6,8-hexahydro-2H-1$\lambda^6$-thia-4,8-diaza-phenanthren-7-one as a yellow solid.

Yield: 0.11 g, 61%

$MH^+=319$.

EXAMPLE 13

In Vitro Assay—Androgen Receptor Filtration Binding Assay

The assay was run on a 96 well plate with each well filled with total reaction volume 150 μL, of a solution containing 5 pmol androgen receptor LBD (Panvera) or 30L of freshly prepared rat cytosol, 0.5 nM [$^3$H] R1881 tracer (NEN), 1.5 μL (10 μM) test compound or vehicle (diluted in 30% DMSO, final concentration of DMSO 0.75%) and 150 μL of TED buffer. (TED buffer contains 10 mM Tris.HCl pH 7.4, 1 mM sodium molybdate (60 mg/250 mL), 1.5 mM EDTA, 1 mM DTT and 10% (v/v) glycerol.)

On day one, the solution containing receptor, tracer and TED buffer was distributed onto a 96 well plate. Diluted test compound or control vehicle was then added to individual wells and the plate incubated ay 4° C. overnight.

On day two, to each well was then added 20 μL human γ-globulin (ICN 823102), prepared at 25 mg/ml in TE pH 8.0 and 55 μL 40% polyethylene glycol 8000 (J T Baker U222-08), prepared in TE pH 8.0. The plate was incubated at 4° C. for 60 minutes. During incubation, the harvester was rinsed with 10% PEG 8000, prepared in TE pH 8.0 and the GF/C Unifilter-96 prewet with 10% PEG. The binding reaction was filtered, the retentate was washed three times with 10% PEG and dried under vacuum for about four minutes, then dried at 50° C. for 5 min and then bottom sealed. 25 μL of Microscint-20 (Packard) was added to the filter wells and top sealed. The plate wells were then counted on a TopCount (Packard).

Representative compounds of the present invention were tested for binding to the androgen receptor according to the procedure described above with results as listed in Table 3. % Inhibition values less that 0% indicate no binding at the 1 μM level. The negative number(s) are a result of experimental error from the low number of counts detected.

TABLE 3

Androgen Receptor Binding Results

| ID # | Binding (μM)* | % Inhibition @ 1 μM** |
|---|---|---|
| 1 | 5.2 | |
| 2 | 4.8 | |
| 3 | | 0.5% |
| 4 | | 14% |
| 5 | 7.2 | |
| 6 | 63 | |
| 7 | | 17% |
| 8 | 12 | |
| 9 | 83 | |
| 10 | 24 | |
| 13 | | -19% |
| 14 | | -18% |

*Panvera receptor data
*Cytosollic receptor data

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of the formula (1a)

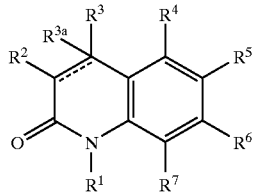

wherein $R^1$ is hydrogen;
$R^2$ is hydrogen;
$R^3$ is halogenated lower alkyl;
$R^{3a}$ is absent or hydroxy;
═══ represents an optional double bond; such that when $R^{3a}$ is absent, the double bond extends from the carbon atom of the ring bound to $R^2$ to the carbon atom of the ring bound to $R^3$;
$R^4$ and $R^5$ are taken together with the carbon atoms to which they are bound to form a six membered, heterocyclyl group containing two heteroatoms selected from the group consisting of O, N and S; wherein the heterocyclyl group is optionally substituted with one to four substituents independently selected from halogen or oxo; provided that when the substituent is oxo, then the substituent is bound to a S atom of the heterocyclyl group;
$R^6$ is hydrogen;
$R^7$ is selected from the group consisting of hydrogen and lower alkyl;
or a pharmaceutically acceptable salt, esteror prodrug thereof.

2. A compound as in claim 1 wherein
$R^1$ is hydrogen;
$R^2$ is hydrogen;
$R^3$ is trifluoromethyl;
$R^{3a}$ is absent or is OH;
═══ represents an optional double bond; such that when $R^{3a}$ is absent, the double bond extends from the carbon atom of the ring bound to $R^2$ to the carbon atom of the ring bound to $R^3$;
$R^4$ and $R^5$ are taken together with the atoms to which they are bound to a heterocyclyl group selected from [1,4]-dioxanyl, 2,2,3,3,-tetrafluoro-[1,4]-dioxanyl, thiomorpholinyl, thiomorpholinyl-1,1-dioxide, thiomorpholinyl-1-oxide and morpholinyl;
$R^6$ is hydrogen;
$R^7$ is selected from the group consisting of hydrogen and methyl;
or a pharmaceutically acceptable salt, ester or prodrug thereof.

3. A pharmaceutical composition comprising a pharmaceutically acceptable carrier and a compound of claim 1.

4. A method of treating a disorder mediated by an androgen receptor, in a subject in need thereof comprising administering to the subject a therapeutically effective amount of the compound of claim 1, wherein the disorder is selected from the group consisting of prostate carcinoma, anorexia nervosa, breast cancer, AIDS, cahexia, male contraception and male performance.

5. A method of treating a condition selected from the group consisting of prostate carcinoma, anorexia nervosa, breast cancer, AIDS, cachexia, male contraception, and male performance, in a subject in need thereof comprising administering to the subject a therapeutically effective amount of the compound of claim 1.

* * * * *